United States Patent [19]

Franz et al.

[11] Patent Number: 4,737,347

[45] Date of Patent: Apr. 12, 1988

[54] MULTI-TUBE REACTOR

[75] Inventors: Volker Franz; Rolg Geissen, both of Frankfurt am Main, Fed. Rep. of Germany

[73] Assignee: Metallgesellschaft Aktiengesellschaft, Frankfurt am Main, Fed. Rep. of Germany

[21] Appl. No.: 889,322

[22] Filed: Jul. 23, 1986

[30] Foreign Application Priority Data

Jul. 27, 1985 [DE] Fed. Rep. of Germany ....... 3526967

[51] Int. Cl.⁴ .......................... F28D 7/00; B01J 10/00; B01J 12/00
[52] U.S. Cl. .............................. 422/197; 165/104.31; 422/201
[58] Field of Search ...................... 422/197, 201, 200; 165/104.31

[56] References Cited

U.S. PATENT DOCUMENTS 3,566,961  3/1971  Lorenz et al. ................... 422/197
3,850,232  11/1974  Wanka et al. .................. 422/197

FOREIGN PATENT DOCUMENTS 1531940  7/1967  France .
2118099  12/1971  France .

Primary Examiner—Barry S. Richman
Assistant Examiner—Joyce L. Woodard
Attorney, Agent, or Firm—Karl F. Ross; Herbert Dubno

[57] ABSTRACT

A multitube reactor for exothermic or endothermic reactions carried out in a multiplicity of tubes, which are surrounded by a liquid, at least part of which is circulated by a circulating pump, which is disposed outside the reactor structure, to flow through heating and cooling means and is the recycled to the reactor structure. The tubes and the surrounding liquid are disposed between a cylindrical inner wall and an outer wall which surrounds and is coaxial to the inner wall. The circulating pump is disposed in the liquid-free space that is surrounded by the inner wall.

3 Claims, 1 Drawing Sheet

MULTI-TUBE REACTOR

FIELD OF THE INVENTION

Our present invention relates to a multi-tube reactor for carrying out exothermic or endothermic reactions in a fluid in a multiplicity of tubes, which are contained in a reactor and are surrounded by a liquid, at least part of which is circulated by a circulating pump through heating or cooling means and which is then recycled to the reactor.

BACKGROUND OF THE INVENTION

Multi-tube reactors of this type are known and have been described in open German Application DE-OS No. 28 46 693 and the corresponding U.S. Pat. No. 4,263,141.

The tubes of the known tubular reactors contain a bulk material consisting of a granular catalyst.

The tubes are formed in concentric circular arrays, and the ratio of the diameters of the outermost and innermost circular arrays varies between 10:1 and 20:1, depending on the design of the reactor structure.

As the liquid used to supply or extract heat flows along the tubes, the liquid must flow past numerous circular arrays of tubes so that a high pressure drop results. Owing to the large difference between the diameters of the inner and outer circular arrays of tubes, the liquids flowing past the inner arrays of tubes have much higher velocities than the heat—transfer liquid flowing past the outer arrays so that the heat transfer rates are highly different.

When it is desired to ensure an adequate heat transfer at the outer tubes, therefore, the liquid must be circulated at a high rate although this will result in an excessively high velocity of flow of the liquid near the inner arrays of tubes so that a high power is required to circulate the liquid and the heat transfer is not uniform too.

In the known multi-tube reactors having a circulating pump external of the reactor shell, the liquid is supplied to the reactor structure through an annular manifold, which is mounted on the outside surface of the reactor structure, and is connected through numerous ports to that space in the reactor structure in which the tubes are disposed. Liquid is returned to the circulating pump through another manifold which is mounted on the outside surface of the reactor structure.

The cross-section areas of the external manifolds must be selected for a flow of liquid at a rate which is one-half of the circulation rate. Also the lines connecting the manifolds to the circulating pump are often rather long. Short lines may be sufficient if two pumps rather than a single pump are used but this involves an undesired additional expenditure.

OBJECTS OF THE INVENTION

It is the principal object of our invention to provide an improved reactor which overcomes these drawbacks.

It is another object of the invention to provide a multi-tube reactor which is so designed that the resistance to the flow of the liquid adjacent to the tubes is low, that the heat is supplied and/or extracted as uniformly as possible, and that the reactor structure and the circulating pump can be short lines.

SUMMARY OF THE INVENTION

These objects are attained in accordance with the invention in that the tubes and the liquid surrounding the tubes are disposed between an approximately cylindrical inner wall and as outer wall, which surrounds and is substantially coaxial to the inner wall, and the circulating pump is disposed in the liquid-free space which is surrounded by the inner wall.

Because the pump is disposed in a liquid-free interior space, the pump is readily accessible from the outside, e.g. for maintenance, through a manhole or opening in the end of the reactor.

In the reactor in accordance with the invention the tubes generally are provided in circular arrays and the ratio of the diameters of the outermost and innermost circular arrays is much smaller than in known multi-tube reactors.

At least one manifold for supplying liquid to the reactor structure and at least one manifold for withdrawing liquid from the reactor structure are preferably mounted on the inner wall of the multi-tube reactor in accordance with the invention.

Advantageously at least two connecting lines for withdrawing liquid are disposed between the reactor structure and the circulating pump. In such an arrangement each of the manifolds is connected to the circulating pump by a plurality of lines, which may form a spider, so that the manifolds can be smaller in cross-section than manifolds provided with only one connecting line each.

In the multi-tube reactor the inner wall is preferably at least 1.2 meters in diameter and the outer wall is advantageously at least 4 meters in diameter. The advantages of the present reactor will be particularly significant in such large reactors. In most cases, the ratio of the diameters of the outer and inner walls is usually between 4:1 and 1.1:1, preferably between 3:1 and 1.5:1. It will be understood that the space surrounded by the inner wall may contain not only the pump but also the heating or cooling means if a compact design is desired.

Thus a multi-tube reactor for carrying out a reaction, can comprise:

a substantially cylindrical outer wall forming a shell enclosing a liquid-containing reactor space;

a substantially cylindrical inner wall spacedly surrounded by the outer wall and defining the liquid-containing space therewith, the liquid-containing space being annular and internally and externally bound by the inner wall and the outer wall respectively, the inner wall surrounding a liquid-free space;

a multiplicity of reactor tubes in the liquid-containing space for effecting a reaction in a fluid traversing said tubes, the tubes being in contact with a liquid received in said liquid-containing space around said tubes;

heat-modifying means for altering the temperature of the liquid; and a circulating pump received in the liquid-free space within the inner wall and connected with the liquid-containing space for circulating said liquid from the liquid-containing space through the heat modifying means.

BRIEF DESCRIPTION OF THE DRAWING

The above and other objects, features and advantages of the invention will become more readily apparent from the following description, reference being made to the accompanying drawing in which.

SPECIFIC DESCRIPTION

Figure 1:
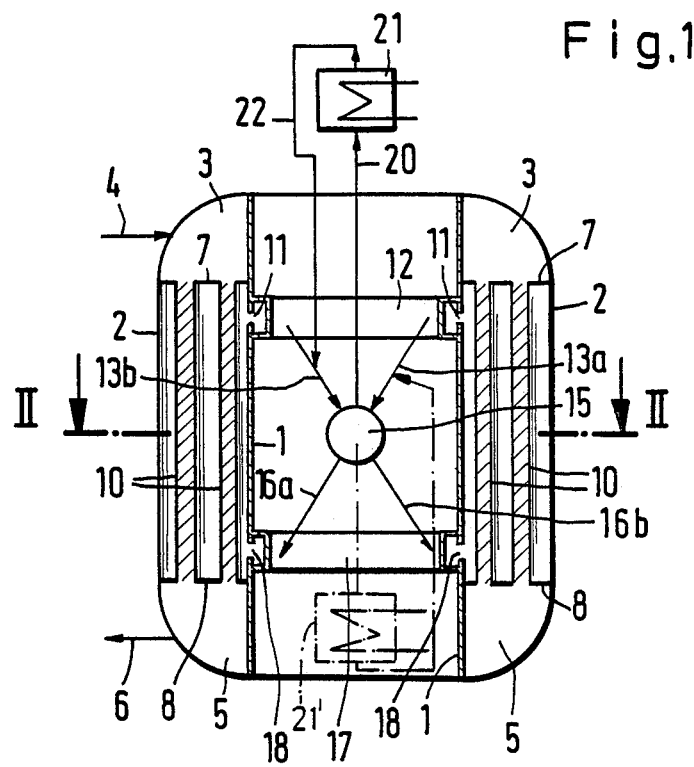
FIG. 1 is a partly diagrammatic longitudinal sectional view showing the reactor.

The reactor structure of the multi-tube reactor comprises a cylindrical inner wall 1 and an outer wall 2, which is coaxial to the inner wall 1. The outer wall has inwardly directed curved top and bottom portions, which are joined to the inner wall 1 and define upper and lower header spaces 3 and 5, respectively. The mixed gases to be interrelated are supplied in a line 4 to the upper headed space 3 and the product is withdrawn in a line 6 from the lower header space 5.

Numerous vertical tubes 10, shown only diagrammatically, are disposed between upper and lower tube plates 7 and 8 and are usually filled with granular catalyst material. In known manner, the mixture to be reacted flows from the upper header space 3 into the tubes 10 and flows through the latter and is subjected to an endothermic or exothermic reaction therein, and the product is withdrawn through the lower header space 5 and the line 6.

Figure 2:
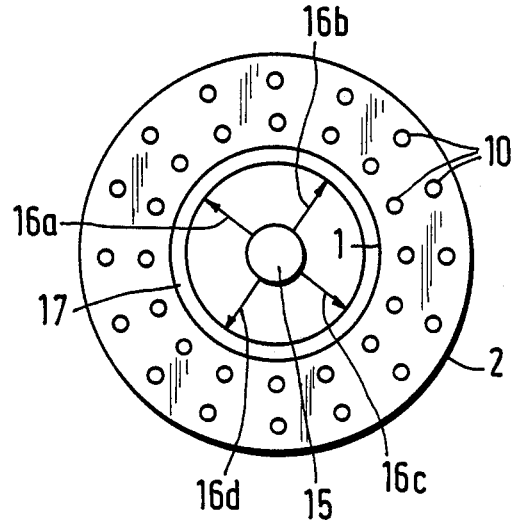
FIG. 2 is a transverse sectional view taken on line II—II in FIG. 1.

For an extraction of heat from the interior of the tubes 10 or for a supply of heat to the interior of the tubes 10, the latter are surrounded by a liquid, which is circulated. From the space between the inner and outer walls 1 and 2, that liquid flows through ports 11 in the inner wall 1 to an upper manifold 12 and from the latter through a plurality of connecting lines 13a and 13b to the circulating pump 15, which is disposed in the liquid-free space that is surrounded by the inner wall 1. A partial stream of liquid which has been drawn through lines 13a and 13b is supplied through the connecting lines 16a, 16b, 16c and 16d, see also FIG. 2, to a lower manifold 17. Like the upper manifold 12, the lower manifold 17 is annular and in contact with the inner wall 1. The lower manifold 12 communicates through ports in the inner wall 18 with that space within the reactor structure which contains the tubes 10. The liquid supplied by the pump 15 enters the reactor structure through the ports 18 and flows around the tubes 10 in contact therewith and is drawn by the circulating pump 15 through the upper manifold 12.

A partial stream of the liquid is continuously delivered by the pump 15 through line 20 to the heat exchanger 21 and is conducted from the heat exchanger 21 through line 22 to the suction side of the pump 15. In the heat exchanger 21, a liquid for supplying heat to the tubes 10 will be heated or a liquid for extracting heat from the tubes 10 will be cooled.

It will be understood that the heat exchanger 21 may also be disposed in the liquid-free space that is surrounded by the inner wall 1, see element 21' in FIG. 1

The liquid may consist, e.g. of water, molten salt, or an organic liquid known per se. In any case the multi-tube reactor is not restricted to the use of a specific liquid. The number of lines connecting the upper manifold 12 to the pump 15 and the number of lines connecting the pump 15 to the lower manifold 17 may be chosen freely and in most cases is between 2 and 6, inclusive, in either case. As shown at 21', the heat modifying unit or another such unit can be inside the liquid—free space.

In the operation of the multi-tube reactor in accordance with the invention, much less energy is required to operate the pump 15 and a more uniform heat transfer is effected between the liquid and the tubes.

Additional advantages reside in that a pump having a given power input can be used to circulate the liquid at a higher rate than in known multi-tube reactors so that the temperature will be more uniformly distributed in the reactor structure in the horizontal and vertical directions. This is essential for numerous processes.

A single circulating pump will be sufficient even for very large reactors.

By way of example may it be mentioned that the reactor may be used to produce phthalic acid anhydride from orthoxylene or naphthalene or for the production of styrene by a dehydrogenation of ethylbenzene.

We claim:

1. A multi-tube reactor for carrying out an endothermic or exothermic reaction, comprising:

a substantially cylindrical outer wall forming a shell enclosing a liquid-containing reactor space;

a substantially cylindrical inner wall spacedly surrounded by said outer wall and defining said liquid-containing reactor space therewith, said liquid-containing space being annular and internally and externally bounded by said inner wall and said outer wall respectively, said inner wall surrounding a liquid-free space;

a multiplicity of reactor tubes in said liquid-containing reactor space for effecting an endothermic or exothermic reaction in a fluid traversing said tubes, said liquid-containing space around said tubes and being provided with means connecting said tubes at one end to a source of a fluid in which the reaction is to be effected and with means connecting said tubes at an opposite end to an outlet for the fluid in which the reaction has been effected;

heat-modifying means for altering the temperature of said liquid, said means being a heater when said reaction is endothermic and said means being a cooler when said reaction is exothermic;

a circulating pump received in said liquid-free space within said inner wall and connected with said liquid-containing reactor space and said heat-modifying means for circulating said liquid from said liquid-containing space through said heat-modifying means and back to said liquid-containing reactor space; and at least two manifolds formed on said inner wall and communicating with said liquid-containing reactor space, each of said manifolds being connected to said pump by at least two pipes for pumping said liquid into said liquid-containing reactor space through one of said manifolds and for withdrawing said liquid from said liquid-containing reactor space through the other of said manifolds, said inner wall having a diameter of at least 1.2 meters, said outer wall having a diameter of at least 4 meters, and the ratio of the diameter of the outer and inner wall being between 3:1 to 1.1:1.

2. The reactor defined in claim 1 wherein said heat-modifying means is located in said liquid-free space.

3. The reactor defined in claim 1 wherein said heat-modifying means is located outside of said outer wall.

* * * * *

UNITED STATES PATENT AND TRADEMARK OFFICE
CERTIFICATE OF CORRECTION

PATENT NO. : 4,737,347
DATED : 12 April 1988
INVENTOR(S) : Volker FRANZ et al

It is certified that error appears in the above-identified patent and that said Letters Patent is hereby corrected as shown below:

Item [75] The second inventor's name is to read:

-- Rolf Geissen --.

Signed and Sealed this

Thirteenth Day of September, 1988

Attest:

DONALD J. QUIGG

Attesting Officer     Commissioner of Patents and Trademarks